(12) United States Patent
Yoneda et al.

(10) Patent No.: US 6,380,229 B1
(45) Date of Patent: Apr. 30, 2002

(54) 2-(N-CYANOIMINO)THIAZOLIDIN-4-ONE DERIVATIVES

(75) Inventors: Fumio Yoneda; Hironori Ohde; Mayumi Watanabe; Takashi Ando; Takuya Yasusa; Yuko Uegaki, all of Osaka (JP)

(73) Assignee: Fujimoto Co., Ltd., Osaka (JP)

( * ) Notice: Subject to any disclaimer, the term of this patent is extended or adjusted under 35 U.S.C. 154(b) by 0 days.

(21) Appl. No.: 09/889,103

(22) PCT Filed: Nov. 12, 1999

(86) PCT No.: PCT/JP99/06352

§ 371 Date: Jul. 11, 2001

§ 102(e) Date: Jul. 11, 2001

(87) PCT Pub. No.: WO01/36402

PCT Pub. Date: May 25, 2001

(51) Int. Cl.[7] .................... A61K 31/426; A61K 31/427; C07D 277/40; C07D 417/10; C07D 417/12

(52) U.S. Cl. .................... 514/369; 548/181; 548/184

(58) Field of Search ................ 548/181, 184; 514/369

(56) References Cited

FOREIGN PATENT DOCUMENTS

| EP | 697410 | 2/1996 |
|---|---|---|
| JP | 7-165371 | 6/1995 |
| JP | 8-92249 | 4/1996 |
| JP | 8-157461 | 6/1996 |
| JP | 9-165371 | 6/1997 |
| JP | 2000-26438 | 1/2000 |

OTHER PUBLICATIONS

Specification, claims and Abstract of Serial No. 09/914,921, filed Sep. 26, 2001.

*Primary Examiner*—Laura L. Stockton

(74) *Attorney, Agent, or Firm*—Wenderoth, Lind & Ponack, L.L.P.

(57) ABSTRACT

This invention provides novel 2-(N-cyanoimino)thiazolidin-4-one derivatives represented by formula I or a pharmaceutically acceptable salt or solvate thereof:

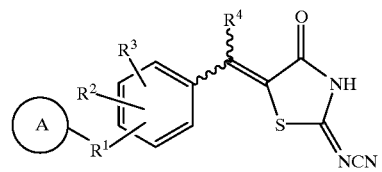

I wherein ring A represents a benzene ring, a condensed ring or a heterocyclic ring, each of which may be substituted by one or more substituents selected from a straight or branched $C_1$–$C_4$ alkyl group, a haloalkyl group, a halogen atom or —$OR^5$, $R^1$ represents a single bond, an oxygen atom, a sulfur atom, a methyne group, a straight or branched $C_1$–$C_4$ alkylene or alkenylene group optionally substituted by a phenyl group, $R^6$—X, X—$R^6$, X—$R^6$—X, $R^6$—X—$R^6$, —C(=O)—$NR^7$— or —$NR^7$—C(=O)—, $R^2$ and $R^3$ are the same or different and each represents a hydrogen atom, a $C_1$–$C_4$ alkyl group, —$OR^8$ or a halogen atom, $R^4$ represents a hydrogen atom or a $C_1$–$C_4$ alkyl group, $R^5$ represents a hydrogen atom or a $C_1$–$C_4$ alkyl group, $R^6$ represents a straight or branched $C_1$–$C_4$ alkylene or alkenylene group, $R^7$ represents a hydrogen atom or a $C_1$–$C_4$ alkyl group, $R^8$ represents a hydrogen atom, a $C_1$–$C_4$ alkyl group or an aralkyl group, X represents an oxygen atom or a sulfur atom.

They have excellent activities of lowering triglyceride and cholesterol levels, and are useful for preventing from and/or treating hyperlipidemia and related complications.

19 Claims, No Drawings

2-(N-CYANOIMINO)THIAZOLIDIN-4-ONE DERIVATIVES

This application is a 371 application of PCT/JP99/06352, filed Nov. 12, 1999.

TECHINICAL FIELD

The invention relates to novel 2-(N-cyanoimino) thiazolidin-4-one derivatives or pharmaceutically acceptable salts or solvates thereof, which have excellent activities in a lowering blood triglyceride level and a cholesterol level, and are useful for prevention from and/or treatment of hyperlipidemia and related complications.

BACKGROUND ART

Many epidemiological studies have shown that hypercholesterolemia is a risk factor for coronary heart disease (CHD). Recently, hypertriglycemia is confirmed to be an independent risk factor for CHD. (J Jpn Atheroscler Soc, 25 (1–2), 1–34 (1997)—Guideline for Diagnosis and Treatment of Hyperlipidernias in Adults).

For the therapy of hypertriglycemia, dextran sulfate sodium, nicotinic acid derivatives, fibric acid derivatives (fibrates) have been used as the first choice. In particular bezafibrate is known to have more potent cholesterol lowering property as well as triglyceride lowering property than the earlier fibrates. And for hypercholesterolemia, HMG-CoA reductase inhibitors (e.g. pravastatin, simvastatin, etc., known as statins) are generally provided for clinical use.

When blood cholesterol level alone is elevated, HMG-CoA reductase inhibitors are employed. However, when both levels of blood cholesterol and triglyceride are elevated or the effect of hypolipidemic agent is not sufficient, some lipid lowering drugs are combined.

Thus, an aim of the present invention is to provide a novel class of potent hypolipidemic agents, which reduce more effectively a blood triglyceride level or both levels of blood triglycerides and cholesterol.

Some antidiabetic agents that are partially analogous to the compounds of the present invention have been found and developed, for example, troglitazone and pioglitazone. However, they are thiazolidin-2,4-dione derivatives, and according to the conference abstract of the 28th Meeting of the Japan Atherosclerosis Society, Osaka,. June, 1996, No.024, pioglitazone did not change total cholesterol and triglyceride levels in hyperlipidemic rabbits. Therefore, from a view of chemical and biological properties, the compounds of the present invention are considered to be different from those antidiabetic compounds.

DISCLOSURE OF INVENTION

This invention provides prophylactic or therapeutic agents for hyperlipidemia and related complications comprising novel 2-(N-cyanoimino)thiazolidin-4-one derivatives represented by formula I or a pharmaceutically acceptable salt or solvate thereof as active ingredients:

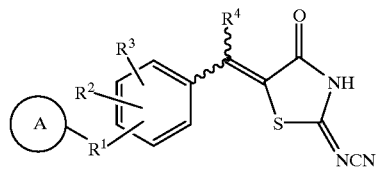

I wherein ring A represents a benzene ring, a condensed ring or a heterocyclic ring, each of which may be substituted by one or more substituents selected from a straight or branched $C_1$–$C_4$ alkyl group, a haloalkyl group, a halogen atom or —$OR^5$;

$R^1$ represents a single bond, an oxygen atom, a sulfur atom, a methyne group, a straight or branched $C_1$–$C_4$ alkylene or alkenylene group optionally substituted by a phenyl group, $R^6$—X, X—$R^6$, X—$R^6$—X, $R^6$—X—$R^6$, —C(=O)—$NR^7$— or —$NR^7$—C(=O)—;

$R^2$ and $R^3$ are the same or different and each represents a hydrogen atom, a $C_1$–$C_4$ alkyl group, —$OR^8$ or a halogen atom, $R^4$ represents a hydrogen atom or a $C_1$–$C_4$ alkyl group;

$R^5$ represents a hydrogen atom or a $C_1$–$C_4$ alkyl group;

$R^6$ represents a straight or branched $C_1$–$C_4$ alkylene or alkenylene group;

$R^7$ represents a hydrogen atom or a $C_1$–$C_4$ alkyl group;

$R^8$ represents a hydrogen atom, a $C_1$–$C_4$ alkyl group or an aralkyl group;

X represents an oxygen atom or a sulfur atom.

The present inventors have carried out various investigations to solve the above problem and found that the novel 2-(N-cyanoimino)thiazolidin-4-one derivatives represented by formula I have excellent blood triglyceride lowering and cholesterol lowering activities. Thus the present invention was successfully established.

BEST MODE FOR CARRYING OUT THE INVENTION

"Salts" refers to low toxic salts derived from sodium, potassium, ammonia or organic amines, for instance.

"$C_1$–$C_4$ alkyl group" refers to methyl, ethyl, n-propyl, iso-propyl, n-butyl or tert-butyl, for instance.

"$C_1$–$C_4$ alkoxy group" refers to methoxy, ethoxy, n-propoxy, iso-propoxy, n-butoxy or tert-butoxy, for instance.

"halogen atom" refers to generally fluorine atom, chlorine atom, bromine atom or iodine atom. More preferably it is fluorine atom or chlorine atom.

"ring A" refers to a benzene ring, a benzodioxole ring, a benzofuran ring, a benzothiazole, a fluorene ring, an indan ring, an indoline ring or a pyridine ring, connecting with $R^1$ at any position, for instance.

Particularly preferred compounds represented by formula I are as follows:

2-(N-Cyanoimino)-5-[(E)-4-stylylbenzylidene]thiazolidin-4-one;

2-(N-Cyanoimino)-5-[(E)-4-(a-methylstylyl)benzylidene]thiazolidin-4-one;

2-(N-Cyanoimino)-5-[4-(benzyloxymethyl)benzylidene]thiazolidin-4-one;

2-(N-Cyanoimino)-5-[(E)-4-(b-methylstylyl)benzylidene]thiazolidin-4-one;

2-(N-Cyanoimino)-5-[4-(3-phenylpropoxy)benzylidene]
thiazolidin-4-one;

2-(N-Cyanoimino)-5-[4-(4-chlorophenoxy)benzylidene]
thiazolidin-4-one;

2-(N-Cyanoimino)-5-(4-phenylthiobenzylidene)
thiazolidin-4-one;

2-(N-Cyanoimino)-5-[(E)-4-(2-fluorostylyl)benzylidene]
thiazolidin-4-one;

2-(N-Cyanoimino)-5-[4-(2,5-dimethylphenoxy)
benzylidene]thiazolidin-4-one;

2-(N-Cyanoimino)-5-(4-phenethyloxybenzylidene)
thiazolidin-4-one;

2-(N-Cyanoimino)-5-[4-(2-phenylpropoxy)benzylidene]
thiazolidin-4-one 2-(N-Cyanoimino)-5-(3-phenethyloxybenzylidene)
thiazolidin-4-one;

2-(N-Cyanoimino)-5-(4-benzyloxybenzylidene)
thiazolidin-4-one;

2-(N-Cyanoimino)-5-[4-(5-chlorobenzofuran-2-yl)
benzylidene]thiazolidin-4-one;

2-(N-Cyanoimino)-5-[(E)-4-(4-methoxystylyl)
benzylidene]thiazolidin-4-one;

2-(N-Cyanoimino)-5-(3-phenoxybenzylidene)
thiazolidin-4-one;

2-(N-Cyanoimino)-5-[4-(1,3-benzodioxol-5-ylmethoxy)
benzylidene]thiazolidin-4-one;

2-(N-Cyanoimino)-5-[4-(4-methylbenzyloxy)
benzylidene]thiazolidin-4-one;

2-(N-Cyanoimino)-5-[4-(4-chlorobenzyloxy)
benzylidene]thiazolidin-4-one;

2-(N-Cyanoimino)-5-[3-methoxy-(E)-4-
stylylbenzylidene]thiazolidin-4-one;, 2-(N-Cyanoimino)-5-(2-phenethyloxybenzylidene)
thiazolidin-4-one;

2-(N-Cyanoimino)-5-(4-phenoxybenzylidene)
thiazolidin-4-one;

2-(N-Cyanoimino)-5-[3-(benzyloxy)benzylidene]
thiazolidin-4-one;

2-(N-Cyanoimino)-5-[4-(benzylthio)benzylidene]
thiazolidin-4-one;

2-(N-Cyanoimino)-5-(4-phenethylbenzylidene)
thiazolidin-4-one;

2-(N-Cyanoimino)-5-[4-[2-(4-chlorophenyl)ethoxy]
benzylidene]thiazolidin-4-one;

2-(N-Cyanoimino)-5-[1-[(E)-4-(4-methoxystylyl)phenyl]
ethylidene]thiazolidin-4-one;

2-(N-Cyanoimino)-5-(4-benzyloxy-2,5-
dimethylbenzylidene)thiazolidin-4-one;

2-(N-Cyanoimino)-5-[(E)-3-stylylbenzylidene]
thiazolidin-4-one;

The compounds of the present invention are novel compounds not described in any literature and can be prepared by the following methods as the example.

A 2-(N-cyanoimino)thiazolidin-4-one represented by formula II or the salts thereof are reacted with an aldehyde or ketone represented by formula III

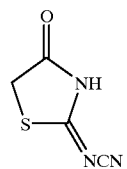

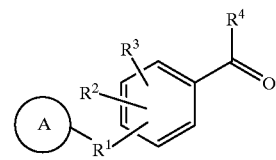

wherein ring A represents a benzene ring, a condensed ring or a heterocyclic ring, each of which may be substituted by one or more substituents selected from a straight or branched $C_1$–$C_4$ alkyl group, a haloalkyl group, a halogen atom or —$OR^5$;

$R^1$ represents a single bond, an oxygen atom, a sulfur atom, a methyne group, a straight or branched $C_1$–$C_4$ alkylene or alkenylene group optionally substituted by a phenyl group, $R^6$—X, X—$R^6$, X—$R^6$—X, $R^6$—X—$R^6$, —C(=O)—$NR^7$— or —$NR^7$—C(=O)—;

$R^2$ and $R^3$ are the same or different and each represents a hydrogen atom, a $C_1$–$C_4$ alkyl group, —$OR^8$ or a halogen atom;

$R^4$ represents a hydrogen atom or a $C_1$–$C_4$ alkyl group;

$R^5$ represents a hydrogen atom or a $C_1$–$C_4$ alkyl group;

$R^6$ represents a straight or branched $C_1$–$C_4$ alkylene or alkenylene group;

$R^7$ represents a hydrogen atom or a $C_1$–$C_4$ alkyl group;

$R^8$ represents a hydrogen atom, a $C_1$–$C_4$ alkyl group or an aralkyl group;

X represents an oxygen atom or a sulfur atom.

The reaction can be carried out in a suitable solvent such as ethanol, acetonitrile, 1,4-dioxane, N,N-dimethylformamide, dimethyl sulfoxide, pyridine, toluene, and xylene, alternatively without employing a solvent, in the presence of ammonium acetate at a temperature ranged from ambient temperature to 200° C., preferably from 70° C. to 150° C., for a period of time between 10 minutes to 10 hours, usually 20 minutes to 5 hours.

There are geometric isomers for the present compounds, however, in solution, reversible isomerization of C5-double bond of thiazolidine occurs very easily by the action of light or heat.

The compounds of the present invention have excellent activities in lowering blood triglyceride and cholesterol levels and are pharmaceutically useful as therapeutic agents for prevention and/or treatment of hyperlipidemia and related complications.

The compounds of the present invention and pharmaceutically acceptable salts thereof can be orally or parenterally administered either alone or preferably in the form of appropriate pharmaceutical compositions such as tablets, powders, granules, capsules, syrups, or injections comprised of pharmaceutically acceptable carriers, diluents, solubilizers, or other pharmaceutical additives.

The dosage will depend on the condition, age, body weight, and other factors of each patient or efficacy of an active ingredient. Generally, when the compound of the present invention is orally administered, the daily dose of the present invention preferably ranges from 10 to 400 mg for adult, and is administered once or in several divided doses a day.

The invention is illustrated by the following examples.

EXAMPLE 1
2-(N-Cyanoimino)-5-[(E)-4-stylylbenzylidene]thiazolidin-4-one

A mixture of 4.48 g (0.025 mol) of 2-(N-cyanoimino) thiazolidin-4-one potassium salt, 5.47 g (0.026 mol) of trans-4-stilbencarboxaldehyde and 2.02 g (0.026 mol) of ammonium acetate in 100 mL of ethanol was heated for 2 hours under reflux. After cooling, ether was added to the reaction mixture and the precipitated potassium salt of the title compound was collected by filtration. To the rapidly stirring suspension of the salt in 50 mL of acetone, 5 mL of conc. hydrogen chloride was added dropwise and then 250 mL of water was added. The precipitate was collected and dried under reduced pressure to yield the title compound.

The structural formula, yield, and the physical property of the compound are shown in Table 1.

EXAMPLE 2 TO EXAMPLE 61

In substantially the same manner as in Example 1, the compounds shown in Table 1 were obtained.

Their structural formulas, yields, and physical properties are shown in Table 1.

Abbreviations used in Table 1 are defined as follows:

| | |
|---|---|
| Ex. | Example |
| mp | melting point |
| recryst solv | recrystallization solvent |
| EI-MS | electron impact ionization mass spectroscopy |
| IR | infrared spectroscopy |
| EA | elemental analysis |
| $^1$H NMR | proton nuclear magnetic resonance spectra |
| s | singlet |
| d | doublet |
| dd | doublet of doublets |
| t | triplet |
| m | multiplet |
| br | broad |
| J | coupling constant |

*1: After heating for 10 minutes at 130° C. without solvent, the soluble part of reaction mixture in chloroform is chromatographed on a silica gel column.
*2: n-Butanol was used as solvent.
*3: E = ethanol, DMF = N,N-dimethylformamide, I = isopropanol, A = acetone, M = methanol, EA = ethyl acetate, H = hexane
*4: Solvent; 10% Pyridine-d5/DMSO-d6

TABLE 1

2-(N-Cyanoimino)thiazolidin-4-ones

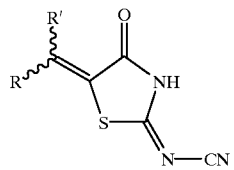

| Ex. No. | Description | Yield (%) | R | R' | mp(°C.) (recryst solv *3) | EI-MS (m/z) |
|---|---|---|---|---|---|---|
| 1 | yellow crystals | 88 | [Ph-CH=CH-C6H4-] | H | 265 (dec) (E-DMF) | 331(M+), 236, 202, 179 |
| 2 | orange-yellow crystals | 84 | [Ph-C(CH3)=CH-C6H4-] | H | 226–227.5 (E-DMF) | 345(M+), 258, 243, 162 |
| 3 | pale yellow crystals | 90 | [Ph-CH2-O-CH2-C6H4-] | H | 170.5–171.5 (E-DMF) | 349(M+), 320, 258, 243, 230, 162, 147, 135, 115, 103, 91, 79, 77 |
| 4 | yellow needles | 66 | [Ph-C(CH3)=CH-C6H4-]* | H | 236.5–237.5 (E-DMF) | 345(M+), 320, 249, 233, 205 |

TABLE 1-continued 2-(N-Cyanoimino)thiazolidin-4-ones

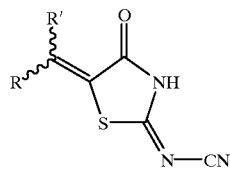

| No. | Appearance | Yield (%) | R, R' structure | R' | mp (°C) (solvent) | MS m/z |
|---|---|---|---|---|---|---|
| 5 | yellow crystals | 78 | 4-(3-phenylpropoxy)phenyl | H | 212.5–213 (dec) (E-DMF) | 363(M+), 272, 268, 245, 176, 150, 121, 91, 65 |
| 6 | orange-yellow needles | 69 | 4-(4-chlorobenzyl)phenyl | H | 225–226.5 (dec) (E-DMF) | 355(M+), 262, 260, 149 |
| 7 | orange crystals | 76 | 4-(phenylthio)phenyl | H | 204.5–205.5 (dec) (E-DMF) | 337(M+), 242, 200, 197, 165 |
| 8 | yellow crystals | 91 | 4-[2-(2-fluorophenyl)ethenyl]phenyl | H | 271–272 (E-DMF) | 349(M+), 254 |
| 9 | orange-yellow plates | 62 | 4-(2,4-dimethylphenoxy)phenyl | H | 196–197.5 (E) | 349(M+), 254, 121, 149, 134, 221, 105, 79 |
| 10 | pale yellow crystals | 78 | 4-(2-phenylethoxy)phenyl | H | 193–194 (dec) (I-DMF) | 349(M+), 150, 105, 79 |
| 11 | pale yellow crystals | 66 | 4-(2-phenylpropoxy)phenyl | H | 190–191 (E-DMF) | 363(M+), 244, 210, 149 |
| 12 | pale yellow crystals | 80 | 3-(2-phenylethoxy)phenyl | H | 172–173 (dec) (E-DMF) | 349(M+), 150, 105 |
| 13 | yellow brown crystals | 60 | 4-(benzyloxy)phenyl | H | 230–231 (dec) (E-DMF) | 335(M+), 149, 121, 91 |

TABLE 1-continued
2-(N-Cyanoimino)thiazolidin-4-ones
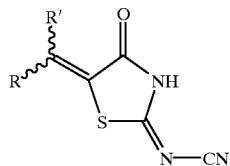
| 14 | yellow needles | 56 | | H 265 (dec) (E-DMF) | 379(M⁺), 286, 284 |
| 15 | yellow crystals | quant. | | H 161–162 (E-DMF) | 361(M⁺), 266, 251, 234, 221, 189, 179, 165, 133, 105, 89, 77 |
| 16 | Light-brown crystals | 93 | | H 202.5–203.5 (E-DMF) | 321(M⁺), 226, 197, 165 |
| 17 | yellow crystals | 95 | | H 217–218 (dec) (E-DMF) | 379(M⁺), 245, 150, 135, 105, 77 |
| 18 | light-orange crystals | 84 | | H 248.5–249.5 (dec) (E-DMF) | 349(M⁺), 150, 105 |
| 19 | orange crystals | 54 | | H 220–221 (dec) (E-DMF) | 369(M⁺), 149, 127, 125, 105 |
| 20 | red crystals | 89 | | H 250.5 (dec) (E-DMF) | 361(M⁺), 262, 234, 223, 206 |
| 21 | yellow crystals | 52 | | H 204–205.5 (dec) (E-DMF) | 349(M⁺), 178, 149, 105, 77 |
| 22 | pale yellow crystals | 84 | | H 218–219 (dec) (E-DMF) | 321(M⁺), 226, 197, 149, 121, 77 |

TABLE 1-continued 2-(N-Cyanoimino)thiazolidin-4-ones

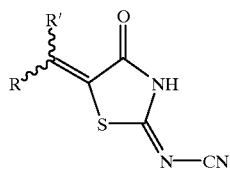

| No. | Appearance | Yield (%) | R | R' | mp (°C) (solvent) | MS m/z |
|---|---|---|---|---|---|---|
| 23 | orange-yellow crystals | 84 | (2-phenethoxy-4-methyl-5-methoxyphenyl... see structure) | H | 195–195.5 (E-DMF) | 379(M$^+$), 274, 180, 105, 79 |
| 24 | pale yellow crystals | 59 | (N-phenyl-4-methylbenzamide structure) | H | 275 (dec) (E-DMF) | 348(M$^+$), 256, 161, 133, 91 |
| 25 | yellow crystals | 79 | (2-(4-methylstyryl)pyridine structure) | H | 295–296 (dec) (DMF) | 331[(M − 1)$^+$], 236, 204, 158, 113, 79, 51 |
| 26 | yellow crystals | 65 | (2,6-dimethoxy-4-methyl-phenethoxy structure) | H | 194–195 (E) | 409(M$^+$), 305, 210, 105, 79 |
| 27 | orange plates | 79 | (N-methyl-N-(4-methylphenyl)benzamide structure) | H | 202.5–203.5 (dec) (E) | 362(M$^+$), 105, 77 |
| 28 | light brown crystals | 95 | (4-bromo-2-fluorobenzyl 4-methylphenyl ether structure) | H | 270–271 (E-DMF) | 433[(M + 2)$^+$], 431(M$^+$), 189, 187, 149, 107 |
| 29 | orange crystals | 65 | (3-(4-methylbenzylidene)-2-indolinone structure) | H | >300 (E-DMF) | 372(M$^+$), 277 |
| 30 | pale yellow crystals | 68 | (2-(4-methylbenzylidene)-1-indanone structure) | H | >300 (DMF) | 371(M$^+$), 276, 247, 213, 139, 114, 89 |

TABLE 1-continued 2-(N-Cyanoimino)thiazolidin-4-ones

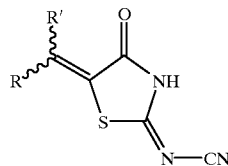

| # | Appearance | Yield | Structure (R) | R' | mp (°C) (solvent) | MS |
|---|---|---|---|---|---|---|
| 31 | yellow crystals | 79 | benzothiazole-CH=CH-C6H4-CH3 | H | >300 (DMF) | 388(M+), 294, 292, 260, 249, 236, 163, 149, 77 |
| 32 | pale yellow crystals | 70 | Ph-CH(C2H5)-O-C6H4-CH3 | H | 144–145.5 (EA-H) | 363(M+), 244, 210, 149 |
| 33 | yellow crystals | 94 | Ph-O-CH2-C6H4-CH3 | H | 238.5–240 (E-DMF) | 335(M+), 250, 240, 173, 147 |
| 34 | yellow crystals | 93 | Ph-C6H4-CH3 | H | 253.5–255 (E-DMF) | 305(M+), 210 |
| 35 | orange crystals | 82 | iPr-C6H4-CH=CH-C6H4-CH3 | H | 240 (dec) (E-A) | 373(M+), 358, 278, 263, 230, 202, 129, 91, 68 |
| 36 | pale yellow crystals | 85 | Ph-CH=CH-CH2-O-C6H4-CH3 | H | 219.5–220.5 (dec) (E-DMF) | 361(M+), 150, 117, 91 |
| 37 | yellow crystals | 37 | Ph-CH2CH2-O, Ph-CH2CH2-O disubst. C6H3-CH3 | H | 161.5–162.5 (E) | 469(M+), 364, 267, 105, 77 |
| 38 | orange-yellow crystals | 73 | Ph-CH2CH2-O-C6H3(OH)-CH3 | H | 189.5–190.5 (dec) (M) | 365(M+), 166, 105, 79 |
| 39 | orange-yellow crystals | 57 | Ph-C(O)-NH-C6H4-CH3 | H | 297 (dec) (E-DMF) | 348(M+), 197, 148, 105 |

TABLE 1-continued 2-(N-Cyanoimino)thiazolidin-4-ones

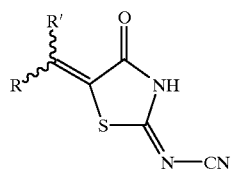

| No. | Appearance | Yield (%) | R,R' | R'' | mp (°C) (solvent) | MS m/z |
|---|---|---|---|---|---|---|
| 40 | orange crystals | 55 | (fluorenylidene-p-tolylmethyl) | H | 257–259 (dec) (E-DMF) | 405(M+), 310, 253, 165 |
| 41 | yellow crystals | 80 | (PhO-CH2CH2-O-C6H4-CH3) | H | 225–226.5 (dec) (E-DMF) | 365(M+), 270, 245, 176, 150, 121, 93, 77 |
| 42 | orange crystals | 76 | (Ph-CH=CH-C6H3(CH3)-OMe) | H | 273–275 (dec) (E-DMF) | 361(M+), 189, 177, 165, 147 |
| 43 | yellow crystals | 76 | (PhCH2CH2-O-C6H3(CH3)-OH) | H | 206–207 (dec) (E) | 365(M+), 166, 105, 79 |
| 44 | brown crystals | 49 | (H5C2, Ph, p-tolyl substituted alkene) | H | 198–200 (E-DMF) | 359(M+), 344, 330, 283, 264, 249, 216, 188, 147, 129, 116, 114, 91 |
| 45 | yellow crystals | 85 | (biphenyl-CH3) | H | 242–243 (E-DMF) | 305(M+), 304, 210, 165 |
| 46 | reddish-brown crystals | 55 | (PhCH2-O-CH2-C6H3(CH3)-OMe) | H | 183.5–185 (E-DMF) | 379(M+), 289, 273, 244, 178, 147, 91 |

TABLE 1-continued 2-(N-Cyanoimino)thiazolidin-4-ones

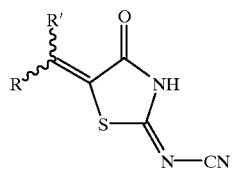

| No. | Appearance | Yield (%) | R | R' | mp (°C) (solvent) | MS m/z |
|---|---|---|---|---|---|---|
| 47 | yellow crystals | 62 | (2,2-diphenyl-1-(4-methylphenyl)ethenyl) | H | 238–239 (E-DMF) | 407(M+), 312, 235, 203 |
| 48 | pale yellow crystals | 71 | (2-(2-(4-methylphenoxy)ethyl)phthalimide) | H | 235–236 (dec) (E-DMF) | 418(M+), 174, 130, 78 |
| 49 | pale yellow crystals | 70 | (benzothiazol-2-ylthio-(4-methylphenyl)methyl) | H | 200–201.5 (E-DMF) | 408(M+), 375, 280, 242, 147, 91 |
| 50 | yellow crystals | 79 | (4-chlorostilbenyl-4'-methyl) | H | >300 (DMF) | 365(M+), 272, 270, 234, 202, 178 |
| 51 | yellow amorphous | 18*1 | (2-(4-methylphenoxy)-1-phenylethyl) | Me | 69–71 | 363(M+), 164 |
| 52 | yellow crystals | 91 | (4-trifluoromethylstilbenyl-4'-methyl) | H | 275–280 (dec) (E-DMF) | 399(M+), 304, 259, 227 |
| 53 | pale yellow crystals | 94 | (3-methyl-benzyloxyphenyl) | H | 201–202.5 (E-DMF) | 335(M+), 245, 177, 149, 121 |
| 54 | yellow crystals | 73 | (benzylthio-(4-methylphenyl)methyl) | H | 282–283 (E-DMF) | 351(M+), 260, 165, 121, 91, 65 |

TABLE 1-continued 2-(N-Cyanoimino)thiazolidin-4-ones

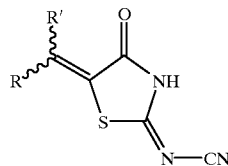

| Ex. No. | Appearance | Yield (%) | Structure (R) | R' | mp (°C) (solvent) | MS |
|---|---|---|---|---|---|---|
| 55 | yellow crystals | 86 | 4-MeC$_6$H$_4$-CH=CH-C$_6$H$_4$- | H | >300 (E-DMF) | 345(M$^+$), 251, 178 |
| 56 | orange crystals | 69 | 4-ClC$_6$H$_4$-CH$_2$CH$_2$-O-C$_6$H$_4$- | H | 206.5–208.5 (E-DMF) | 383(M$^+$), 244, 149, 139 |
| 57 | yellow crystals | 79 | PhCH$_2$O-(2-Me,4-Cl)C$_6$H$_3$- | H | 190–191 (E) | 369(M$^+$), 185, 183, 91 |
| 58 | pale yellow crystals | 64 | Ph-CH$_2$CH$_2$-C$_6$H$_4$- | H | 212–214 (E-DMF) | 333(M$^+$), 242, 147, 91 |
| 59 | yellow crystals | 45 | Ph-CH=CH-(3-Me)C$_6$H$_4$- | H | 247–248 (E-DMF) | 331(M$^+$), 236, 203, 147, 103 |
| 60 | orange-yellow crystals | 80 | PhCH$_2$O-(2,4,5-Me$_3$)C$_6$H$_2$- | H | 227–228 (dec) (E-A) | 363(M$^+$), 177, 91 |
| 61 | yellow-brown crystals | 83*$^2$ | 4-MeOC$_6$H$_4$-CH=CH-C$_6$H$_4$- | Me | 203–204 (E-DMF) | 375(M$^+$), 280, 266, 250, 232, 221, 210, 166 |

| Ex. No. | IR (KBr, cm$^{-1}$) | $^1$H-NMR(DMSO-d6, δ:ppm) | Molecular formula (Molecular weight) | EA(%) Calcld./Found |
|---|---|---|---|---|
| 1 | 3015, 2920, 2740, 2185, 1725, 1580, 1505, 1490, 1340, 1290, 1170, 580, 540, 500 | 5.80–7.00(1H, br), 7.20–8.10(11H, m), 7.86(1H, s) | C$_{19}$H$_{13}$N$_3$OS (331.399) | H 3.95, C 68.86, N 12.68 / H 4.15, C 68.94, N 12.40 |
| 2 | 3150, 3080, 2925, 2210, 1724, 1580, 1360, 1348, 1180, 742, 700, 588, 525 | 2.27(3H, br), 3.50–4.40(1H, br), 7.08(1H, br), 7.20–7.55(5H, m), 7.60–7.80(4H, m), 7.88(1H, s) | C$_{20}$H$_{15}$N$_3$OS (345.426) | H 4.38, C 69.54, N 12.16 / H 4.59, C 69.51, N 11.99 |

TABLE 1-continued 2-(N-Cyanoimino)thiazolidin-4-ones

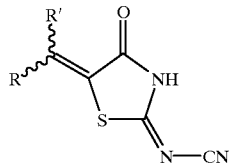

| | | | | |
|---|---|---|---|---|
| 3 | 3200, 3110, 2200, 1740, 1600, 1350, 1307, 1250, 1200, 1190, 1146, 830, 755, 562, 540 | 3.86(1H, br), 4.57(2H, s), 4.62(2H, s), 7.37(5H, s), 7.60(4H, s), 7.87(1H, s) | $C_{19}H_{15}N_3O_2S$ (349.414) | H 4.33, C 65.31, N 12.03 H 4.64, C 65.54, N 11.70 |
| 4 | 2950, 2200, 1717, 1598, 1360, 1293, 1248, 1202, 1181, 763, 721, 700, 582, 542, 520 | 2.28(3H, s), 6.05(1H, br), 6.81(1H, s), 7.20–7.80(9H, m), 7.84(1H, s) | $C_{20}H_{15}N_3OS$ (345.426) | H 4.38, C 69.54, N 12.16 H 4.65, C 69.62, N 11.76 |
| 5 | 3110, 3050, 2925, 2780, 2190, 1690, 1585, 1555, 1500, 1490, 1350, 1260, 1245, 1205, 1170, 1110, 820, 720, 535 | 1.50–2.37(2H, m), 2.37–2.91(2H, m), 4.01(2H, t, J=6Hz), 7.05(2H, d, J=8.5Hz), 7.22(5H, s), 7.54(2H, d, J=8.5Hz), 7.76(1H, s) | $C_{20}H_{17}N_3O_2S$ (363.441) | H 4.71, C 66.10, N 11.56 H 4.85, C 66.05, N 11.53 |
| 6 | 3160, 3075, 2945, 2770, 2200, 1720, 1590, 1580, 1500, 1480, 1355, 1290, 1245, 1205, 1190, 1170, 1090, 1010, 830, 545, 490 | 6.40–8.00(1H, br), 7.13 (4H, dd, J=8.5Hz, 9Hz), 7.49(2H, d, J=9Hz), 7.67 (2H, d, J=8.5Hz), 7.84(1H, s) | $C_{17}H_{10}ClN_3O_2S$ (355.805) | H 2.83, C 57.39, N 11.81 H 3.13, C 57.44, N 11.54 |
| 7 | 3125, 3040, 2930, 2750, 2200, 1730, 1700, 1615, 1600, 1580, 1545, 1490, 1470, 1405, 1355, 1320, 1300, 1185, 1080, 755, 715, 700 | 4.30–5.40(1H, br), 7.21(2H, d, J=9Hz), 7.40(5H, s), 7.50(2H, d, J=9Hz), 7.71(1H, s) | $C_{17}H_{11}N_3OS_2$ (337.427) | H 3.29, C 60.51, N 12.45 H 3.57, C 60.27, N 12.38 |
| 8 | 3050, 2960, 2800, 2200, 1700, 1580 1357, 1296, 1211, 1177, 754, 550 | 3.93(1H, br), 7.20–7.84(10H, m), 7.87(1H, s) | $C_{19}H_{12}FN_3OS$ (349.388) | H 3.46, C 65.32, N 12.03 H 3.73, C 65.53, N 11.78 |
| 9 | 3050, 2950, 2770, 2190, 1735, 1705, 1590, 1500, 1425, 1350, 1290, 1250, 1235, 1195, 1165, 1110, 830, 725 | 2.09, 2.27(each 3H, s), 6.30–8.50(1H, br), 6.85(1H, s), 6.99(1H, d, J=7Hz, 2H, d, J=8.5Hz), 7.24(1H, d, J=7Hz3-H), 7.62(1H, d, J=8.5Hz), 7.82(1H, s) | $C_{19}H_{15}N_3O_2S$ (349.414) | H 4.33, C 65.31, N 12.03 H 4.50, C 64.91, N 11.66 |
| 10 | 3050, 2920, 2750, 2175, 1725, 1580, 1505, 1495, 1345, 1305, 1290, 1255, 1020, 535 | 3.08(2H, t, J=7Hz), 4.30(2H, t, J=7Hz), 6.30–8.30(1H, br), 7.12(2H, d, J=8Hz), 7.33(5H, s), 7.60(2H, d, J=8Hz), 7.82(1H, s) | $C_{19}H_{15}N_3O_2S$ (349.414) | H 4.33, C 65.31, N 12.03 H 4.45, C 65.27, N 11.93 |
| 11 | 2940, 2210, 1730, 1600, 1517, 1360, 1268, 1180, 1019, 777, 742, 706, 561, 548 | 1.34(3H, d, J=6.6Hz), 3.00–3.50(1H, m), 4.17(2H, d, J=6.6Hz), 5.10(1H, br), 7.09(2H, d, J=9Hz), 7.31(5H, s), 7.58(2H, d, J=9Hz), 7.80(1H, s) | $C_{20}H_{17}N_3O_2S$ (363.441) | H 4.71, C 66.10, N 11.56 H 4.76, C 65.76, N 11.57 |
| 12 | 3050, 3020, 2930, 2775, 2220, 1720, 1620, 1600, 1490, 1350, 1290, 1220, 1060, 1030, 990, 780, 750, 730, 700, 525 | 3.05(2H, t, J=7Hz), 4.24 (2H, t, J=7Hz), 6.85–7.60(9H, m), 7.82(1H, s) | $C_{19}H_{15}N_3O_2S$ (349.414) | H 4.33, C 65.31, N 12.03 H 4.53, C 65.64, N 11.96 |
| 13 | 3130, 3070, 2960, 2790, 2215, 1710, 1600, 1590, 1510, 1365, 1260, 1240, 1210, 1180, 985, 840, 765, 730, 595, 510 | 3.80–4.90(1H, br), 5.19(2H, s), 7.18(2H, d, J=9Hz), 7.42(5H, s), 7.60(2H, d, J=9Hz), 7.81(1Hm s) | $C_{18}H_{13}N_3O_2S$ (335.387) | H 3.90, C 64.46, N 12.53 H 4.20, C 64.52, N 12.20 |
| 14 | 3050, 2930, 2750, 2195, 1715, 1595, 1495, 1445, 1415, 1350, 1330, 1290, 1260, 1240, 1165, 1060, 1035, 800, 720, 560, 540 | 7.33(1H, dd, J=9Hz, 2.5Hz), 7.46–7.83(6H, m), 8.03(2H, d, J=8Hz) | $C_{19}H_{10}ClN_3O_2S$ (379.827) | H 2.65, C 60.09, N 11.06 H 3.06, C 60.51, N 10.91 |
| 15 | 3050, 2940, 2750, 2210, 1728, 1583, 1512, 1328, 1292, 1244, 1176, 1022, 969, 839, 800, 707, 633, 560, 542 | 3.81(3H, s), 6.87–7.90(11H, m)*4 | $C_{20}H_{15}N_3O_2S·½H_2O$ (370.433) | H 4.35, C 64.85, N 11.34 H 4.23, C 64.87, N 11.29 |
| 16 | 3025, 2920, 2750, 2200, 1733, 1630, 1600, 1485, 1340, 1286, 1260, 1220, 754, 720, 525 | 5.18(1H, br), 7.00–7.68(9H, m), 7.86(1H, s) | $C_{17}H_{11}N_3O_2S$ (321.36) | H 3.45, C 63.54, N 13.08 H 3.72, C 63.61, N 12.80 |
| 17 | 3050, 2950, 2775, 2200, 1700, 1585, 1510, 1445, 1355, 1300, 1255, 1215, 1175, 1040, 1020, 985, 930, 830, 810, 730, 550 | 3.60–4.70(1H, br), 5.05(2H, s), 5.95(2H, s), 6.80–7.05(3H, m), 7.13(2H, d, J=9Hz), 7.58 (2H, d, J=9Hz), 7.68(1H, s) | $C_{19}H_{13}N_3O_4S$ (379.396) | H 3.45, C 60.15, N 11.08 H 3.74, C 59.82, N 10.96 |
| 18 | 3030, 2930, 2770, 2225, 2200, 1715, 1600, 1590, 1505, 1355, 1290, 1260, 1240, 1190, 1170, 990, 835, 800, 725, 555, 540, 480 | 2.31(3H, s), 4.60–6.20(1H, br), 5.13(2H, s), 7.00–7.47(6H, m), 7.60(2H, d, J=9Hz), 7.80(1H, s) | $C_{19}H_{15}N_3O_2S$ (349.414) | H 4.33, C 65.31, N 12.03 H 4.52, C 65.40, N 11.78 |
| 19 | 3050, 2930, 2780, 2225, 1720, 1620, 1610, 1595, 1510, 1360, 1290, 1260, 1245, 1200, 1175, 1000, 850, 840, 820, 720, 540, 510 | 3.90–5.00(1H, br), 5.20(2H, s), 7.19(2H, d, J=9Hz), 7.48(4H, s), 7.63(2H, d, J=9Hz), 7.82(1H, s) | $C_{18}H_{12}ClN_3O_2S$ (369.832) | H 3.27, C 58.46, N 11.36 H 3.52, C 58.65, N 11.09 |
| 20 | 3030, 2950, 2203, 1744, 1593, 1516, 1360, 1330, 1279, 1161, 1043, 970, 839, 763, 698, 637, 604, 555, 520 | 3.92(1H, d), 4.22(1H, br), 7.09–7.99(10H, m), 7.85(1H, s) | $C_{20}H_{15}N_3O_2S$ (361.425) | H 4.18, C 66.47, N 11.63 H 4.35, C 66.71, N 11.35 |
| 21 | 3010, 2910, 2760, 2200, 1725, 1620, | 3.05(2H, t, J=6.5Hz), | $C_{19}H_{15}N_3O_2S$ | H 4.33, C 65.31, N 12.03 |

TABLE 1-continued 2-(N-Cyanoimino)thiazolidin-4-ones

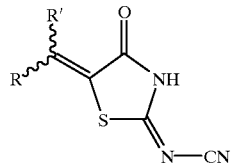

| | | | | |
|---|---|---|---|---|
| | 1610, 1590, 1480, 1445, 1345, 1290, 1280, 1230, 1180, 1150, 750, 720, 690, 520 | 4.25(2H, t, J=6.5Hz), 6.85–7.60(9H, m), 8.01(1H, s) | (349.414) | H 4.48, C 65.34, N 12.09 |
| 22 | 3500–2700, 2200, 1730, 1580, 1505, 1490, 1360, 1295, 1260, 1200, 1170, 745, 530, 480 | 4.00–4.80(1H, br), 7.00–7.53(7H, m), 7.66(2H, d, J=9Hz), 7.84(1H, s) | $C_{17}H_{11}N_3O_2S$ (321.36) | H 3.45, C 63.53, N 13.08 H 3.79, C 63.69, N 12.93 |
| 23 | 3050, 2950, 2790, 2195, 1720, 1700, 1590, 1580, 1510, 1435, 1340, 1270, 1250, 1220, 1170, 1145, 1020, 720, 545, 485 | 3.06(2H, t, J=7Hz), 3.83(3H, s), 4.22(2H, t, J=7Hz), 6.95–7.50(8H, m), 7.77(1H, s) | $C_{20}H_{17}N_3O_3S$ (379.44) | H 4.52, C 63.31, N 11.07 H 4.73, C 63.64, N 11.00 |
| 24 | 3050, 2950, 2770, 2190, 1735, 1650, 1595, 1530, 1500, 1440, 1345, 1320, 1295, 1240, 1180, 770, 720, 690, 585, 565, 540 | 4.15–5.40(2H, br), 6.95–7.62(3H, m), 7.62–8.30(7H, m) | $C_{18}H_{12}N_4O_2S$ (348.386) | H 3.47, C 62.06, N 16.08 H 3.71, C 62.11, N 15.92 |
| 25 | 3050, 2925, 2900–2300, 2175, 1730, 1640, 1610, 1510, 1470, 1425, 1320, 1300, 1270, 1250, 1210, 1175, 980, 820, 600, 545 | 7.30–8.90(m) | $C_{18}H_{12}N_4OS \cdot 1/3 H_2O$ (338.392) | H 3.77, C 63.89, N 16.56 H 4.03, C 63.70, N 16.32 |
| 26 | 3050, 3025, 2940, 2830, 2760, 2195, 1730, 1700, 1600, 1500, 1450, 1420, 1320, 1240, 1185, 1155, 1130, 990, 730, 700, 560, 545, 530 | 2.97(2H, t, J=7Hz), 3.81(6H, s), 4.18(2H, t, J=7Hz), 6.90(2H, s), 7.10–7.40(5H, m), 7.80(1H, s) | $C_{21}H_{19}N_3O_4S$ (409.466) | H 4.68, C 61.60, N 10.26 H 4.75, C 61.64, N 10.19 |
| 27 | 3050, 2935, 2755, 2195, 1730, 1600, 1515, 1350, 1300, 1290(sh), 1245, 1180, 1105, 720 | 3.42(3H, s), 5.50–6.40(1H, br), 7.28(1H, s), 7.30(2H, d, J=8Hz), 7.54(2H, d, J=8Hz), 7.78(1H, s) | $C_{19}H_{14}N_4O_2S \cdot 1/2 C_2H_5OH$ (385.448) | H 4.45, C 62.32, N 14.54 H 4.56, C 62.19, N 14.16 |
| 28 | 3060, 2940, 2800, 2230, 1720, 1635, 1618, 1600, 1520, 1361, 1298, 1273, 1255, 1180, 1002, 897, 852, 840, 540 | 3.62(1H, br), 5.22(2H, s), 7.23(2H, d, J=9Hz), 7.42–7.78(5H, m), 7.83(1H, s) | $C_{18}H_{11}BrFN_3O_2S$ (432.273) | H 2.56, C 50.01, N 9.72 H 2.87, C 50.22, N 9.68 |
| 29 | 3320, 3050, 2940, 2750, 2190, 1720, 1690, 1640, 1590, 1465, 1380, 1345, 1330, 1290, 1245, 1190, 1100, 795, 760, 725, 600, 525 | | $C_{20}H_{12}N_4O_2S \cdot 1/2 C_3H_7NO$ (408.956) | H 3.82, C 63.15, N 15.41 H 4.12, C 62.96, N 15.40 |
| 30 | 3050, 2930, 2770, 2190, 1730, 1690, 1610, 1590, 1505, 1415, 1345, 1325, 1290, 1265, 1240, 1195, 1180, 1090, 735, 720, 600, 540 | | $C_{21}H_{13}N_3O_2S$ (371.42) | H 3.53, C 67.91, N 11.31 H 3.88, C 68.11, N 11.12 |
| 31 | 3050, 3020, 2950, 2750, 2190, 1725, 1595, 1510, 1415, 1350, 1320, 1290, 1240, 1190, 1175, 760, 720, 565, 550 | 7.40–8.50(m) | $C_{20}H_{12}N_4OS_2 \cdot 1/3 C_3H_7NO$ (412.84) | H 3.50, C 61.10, N 14.70 H 3.71, C 61.02, N 14.57 |
| 32 | 2960, 2930, 2200, 1730, 1598, 1507, 1357, 1259, 1177, 1000, 978, 829, 705, 523 | 0.90(3H, t, J=7.2Hz), 1.61–2.10(2H, m), 4.40(1H, br), 5.35(1H, t, J=6.2Hz), 7.05(2H, d, J=8.4Hz), 7.33(5H, s), 7.50(2H, d, J=8.4Hz), 8.73(1H, s) | $C_{20}H_{17}N_3O_2S$ (363.441) | H 4.71, C 66.10, N 11.56 H 4.89, C 66.00, N 11.38 |
| 33 | 3040, 2945, 2770, 2205, 1730, 1603, 1498, 1358, 1338, 1300, 1250, 1180, 810, 753, 514 | 5.19(2H, s), 5.53(1H, br), 6.94–7.53(5H, m), 7.63(4H, s), 7.86(1H, s) | $C_{18}H_{13}N_3O_2S$ (335.387) | H 3.91, C 64.46, N 12.53 H 4.07, C 64.44, N 12.17 |
| 34 | 3045, 2950, 2750, 2200, 1737, 1595, 1490, 1339, 1179, 770, 640, 560, 547 | 4.32(1H, br), 7.33–7.95(9H, m), 7.91(1H, s) | $C_{17}H_{11}N_3OS$ (305.361) | H 3.63, C 66.87, N 13.76 C 66.93, H 3.96, N 13.70 |
| 35 | 3020, 2955, 2760, 2200, 1730, 1585, 1510, 1340, 1295, 1245, 1190, 1170, 830, 555 | 1.20(6H, d, J=7Hz), 2.92(1H, septet), 3.60–4.50(1H, br), 7.15–7.90(11H, m) | $C_{22}H_{19}N_3OS$ (373.48) | H 5.13, C 70.75, N 11.25 H 5.29, C 70.81, N 11.21 |
| 36 | 3100, 3050, 2950, 2780, 2195, 1710, 1590, 1580, 1560, 1510, 1360, 1250, 1205, 1175, 1000, 970, 835, 730, 550 | 3.50–5.00(1H, br), 4.83(2H, d, J=5 Hz), 6.45–6.80(2H, m), 7.18(2H, d, J=9Hz), 6.90–7.80(5H, m), 7.63 (2H, d, J=9Hz, 2, 6-H), 7.82(1H, s) | $C_{20}H_{15}N_3O_2S$ (361.425) | H 4.19, C 66.50, N 11.63 H 4.40, C 66.46, N 11.41 |
| 37 | 3050, 3005, 2930, 2750, 2190, 1720, 1590, 1500, 1460, 1345, 1300, 1270, 1250, 1210, 1165, 1135, 1010, 745, 715, 690 | 3.04(4H, t, J=6.5Hz), 4.00–4.45(4H, m), 6.90–7.60(13H, m), 7.78(1H, s) | $C_{27}H_{23}N_3O_3S$ (469.565) | H 4.94, C 69.06, N 8.95 H 5.09, C 69.02, N 8.64 |
| 38 | 3050, 2930, 2770, 2200, 1720(sh), 1710, 1595, 1505, 1455, 1360, 1280, 1250, 1210, 1170, 1135, 1010, 720, 700, 510 | 3.09(2H, t, J=7Hz), 4.27(2H, t, J=7Hz), 6.90–7.55(8H, m), 7.71(1H, s) | $C_{19}H_{15}N_3O_3S$ (365.413) | H 4.14, C 62.45, N 11.50 H 4.30, C 62.16, N 11.13 |
| 39 | 3060, 2950, 2930, 2770, 2195, 1720, 1705, 1655, 1590, 1510, 1485, 1415, 1350, 1320, 1295, 1240, 1185, 710, | 7.40–8.20(m) | $C_{18}H_{12}N_4O_2S$ (348.386) | H 3.47, C 62.06, N 16.08 H 3.74, C 62.12, N 15.86 |

TABLE 1-continued 2-(N-Cyanoimino)thiazolidin-4-ones

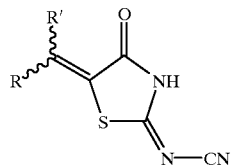

| | | | | |
|---|---|---|---|---|
| | 630, 610, 535 | | | |
| 40 | 3050, 2950, 2760, 2200, 1715, 1595, 1445, 1350, 1290, 1240, 1190, 1170, 775, 730, 610, 540 | 3.50–4.35(1H, br), 6.95–8.15(14H, m) | $C_{25}H_{15}N_3OS \cdot C_2H_5OH$ (451.55) | H 4.69, C 71.82, N 9.31 H 4.80, C 72.12, N 9.18 |
| 41 | 3120, 3060, 2945, 2780, 2190, 1710, 1600, 1505, 1485, 1450, 1360, 1260, 1250, 1230, 1200, 1170, 1065, 955, 830, 760, 725, 540 | 4.37(4H, br), 6.80–7.47(7H, m), 7.47–7.75(3H, m)[*4] | $C_{19}H_{15}N_3O_3S$ (365.413) | H 4.14, C 62.45, N 11.50 H 4.32, C 62.39, N 11.44 |
| 42 | 3045, 2975, 2210, 1710, 1600, 1512, 1365, 1282, 1252, 1219, 1199, 1036, 970, 823, 730, 540 | 3.93(3H, s), 5.25(1H, br), 7.11–7.92(10H, m), 7.93(1H, s) | $C_{20}H_{15}N_3O_2S$ (361.425) | H 4.18, C 66.47, N 11.63 H 4.44, C 66.43, N 11.27 |
| 43 | 3050, 2940, 2760, 2195, 1705, 1570, 1510, 1350, 1300, 1285, 1220, 1190, 1125, 720, 695 | 3.10(2H, t, J=7Hz), 4.27(2H, t, J=7Hz), 6.90–7.60(8H, m), 7.79(1H, s) | $C_{19}H_{15}N_3O_3S$ (365.413) | H 4.14, C 62.45, N 11.50 H 4.28, C 62.26, N 11.33 |
| 44 | 3050, 2955, 2760, 2200, 1733, 1597, 1350, 1297, 1223, 1190, 700 | 1.01(3H, t, J=7Hz), 2.52(2H, m), 4.19(1H, br), 6.54(1H, s), 6.92–7.69(9H, m), 7.73(1H, s) | $C_{21}H_{17}N_3OS$ (359.453) | H 4.77, C 70.17, N 11.69 H 4.96, C 70.15, N 11.52 |
| 45 | 3130, 3060, 2980, 2200, 1703, 1604, 1594, 1353, 1240, 760, 720, 700, 542 | 5.43(1H, br), 7.38–7.93(9H, m), 7.96(1H, s) | $C_{17}H_{11}N_3OS$ (305.361) | H 3.63, C 66.87, N 13.76 H 3.99, C 66.96, N 13.49 |
| 46 | 3080, 2955, 2205, 1735, 1597, 1502, 1363, 1274, 1205, 1140, 1110, 1037, 742, 560, 493 | 3.87(3H, s), 4.56(2H, s), 4.62(2H, s), 7.04–7.71(8H, m), 7.80(1H, s), | $C_{20}H_{17}N_3O_3S$ (379.44) | H 4.52, C 63.31, N 11.07 H 4.64, C 63.20, N 10.79 |
| 47 | 3050, 2200, 1736, 1600, 1500, 1343, 1330, 1297, 1188, 772, 707, 640, 616, 550 | 4.55(1H, br), 6.89–7.60(15H, m), 7.77(1H, s) | $C_{25}H_{17}N_3OS$ (407.497) | H 4.20, C 73.69, N 10.31 H 4.47, C 73.83, N 10.00 |
| 48 | 3050, 2950, 2760, 2195, 1770, 1710, 1590, 1510, 1390, 1350, 1250, 1170, 1120, 720 | 3.90–4.50(4H, m), 7.04(2H, d, J=8.5Hz), 7.53(2H, d, J=8.5Hz), 7.60(1H, s), 7.88(4H, s)[*4] | $C_{21}H_{14}N_4O_4S$ (418.433) | H 3.37, C 60.28, N 13.39 H 3.62, C 60.27, N 13.10 |
| 49 | 3060, 2930, 2750, 2190, 1730, 1640, 1600, 1455, 1430, 1350, 1295, 1245, 1195, 1180, 1000, 760, 715, 545 | 4.71(2H, s), 7.18–7.80(8H, m), 7.80–8.10(2H, m)[*4] | $C_{19}H_{12}N_4OS_3$ ⅔$C_3H_7NO$ (459.26) | H 3.67, C 55.16, N 14.30 H 3.75, C 55.46, N 14.00 |
| 50 | 3040, 2930, 2760, 2220, 1736, 1617, 1590, 1357, 1298, 1181, 1094, 838, 734, 538 | 3.92(1H, br), 7.20–7.87(10H, m), 7.83(1H, s) | $C_{19}H_{12}ClN_3OS$ (365.844) | H 3.31, C 62.38, N 11.49 H 3.53, C 62.48, N 11.46 |
| 51 | 3070, 2950, 2200, 1722, 1600, 1515, 1342, 1250, 1178, 1020, 836, 754, 700, 540 | 2.67(3H, s), 3.06(2H, t, J=6Hz), 3.86(1H, br), 4.28(2H, t, J=6Hz), 7.06(2H, d, J=9Hz), 7.30(5H, s), 7.46(2H, d, J=9Hz) | $C_{20}H_{17}N_3O_2S \cdot ¼H_2O$ (367.945) | H 4.79, C 65.29, N 11.42 H 4.86, C 65.47, N 11.02 |
| 52 | 3050, 2940, 2770, 2220, 1740, 1620, 1600, 1323, 1300, 1180, 1121, 1070, 838, 727, 526 | 4.40(1H, br), 7.45(2H, s), 7.50–7.90(8H, m), 7.83(1H, s) | $C_{20}H_{12}F_3N_3OS$ (399.393) | H 3.03, C 60.15, N 10.52 H 3.25, C 60.28, N 10.63 |
| 53 | 3030, 2920, 2770, 2210, 2200, 1720, 1630, 1612, 1491, 1424, 1357, 1300, 1226, 1023, 786, 740, 723, 525 | 5.18(2H, s), 5.70(1H, br), 7.02–7.65(9H, m), 7.80(1H, s) | $C_{18}H_{13}N_3O_2S$ (335.387) | H 3.91, C 64.46, N 12.53 H 4.09, C 64.35, N 12.37 |
| 54 | 3060, 2960, 2790, 2200, 1700, 1592, 1577, 1541, 1494, 1408, 1358, 1300, 1254, 1192, 1089, 832, 814, 723, 589, 570, 554, 525, 437 | 3.60(1H, br), 4.32(2H, s), 7.15–7.58(9H, m), 7.77(1H, s) | $C_{18}H_{13}N_3OS_2$ (351.454) | H 3.73, C 61.52, N 11.96 H 3.97, C 61.53, N 12.04 |
| 55 | 3090, 2200, 1720, 1589, 1519, 1352, 1300, 1178, 978, 826, 730, 550 | 2.32(3H, s), 5.13(1H, s), 7.10–7.73(11H, m)[*4] | $C_{20}H_{15}N_3OS$ (345.426) | H 4.38, C 69.54, N 12.16 H 4.66, C 70.12, N 11.48 |
| 56 | 3060, 2950, 2760, 2180, 1727, 1587, 1510, 1262, 1179, 1018, 826, 797, 723, 540 | 3.08(2H, t, J=6.8Hz), 4.30(2H, t, J=6.8Hz), 4.30(1H, br), 7.13(2H, d, J=9Hz), 7.38(4H, s), 7.62(2H, d, J=9Hz), 7.83(1H, s) | $C_{19}H_{14}ClN_3O_2S$ (383.859) | H 3.68, C 59.45, N 10.95 H 3.87, C 59.67, N 10.65 |
| 57 | 3175, 3100, 3080, 3040, 2950, 2770, 2200, 1740, 1593, 1585, 1487, 1460, 1350, 1294, 1252, 1220, 1179, 1027, 935, 750, 742, 721, 550 | 3.80–5.80(1H, br), 5.26(2H, s), 7.10–7.70(8H, m), 7.91(1H, s) | $C_{18}H_{12}ClN_3O_2S$ (369.832) | H 3.27, C 58.46, N 11.36 H 3.49, C 58.35, N 10.98 |
| 58 | 3110, 3060, 3030, 2960, 2775, 2200, 1505, 1600, 1588, 1352, 1299, 1251, 1198, 1175, 760, 728, 700 | 2.92(4H, s), 7.00–7.70(9H, m), 7.82(1H, s) | $C_{19}H_{15}N_3OS$ (333.415) | H 4.53, C 68.45, N 12.60 H 4.72, C 68.70, N 12.37 |
| 59 | 3120, 3078, 3055, 3024, 2966, 2790, 2200, 1729, 1705, 1609, 1590, 1355, 1314, 1294, 1265, 1245, 1225, 1200, 1165, 960, 788, 755, 720, 689, 528 | 5.30–6.40(1H, br), 7.10–8.00(12H, m) | $C_{19}H_{13}N_3OS$ (331.399) | H 3.95, C 68.86, N 12.68 H 4.24, C 68.90, N 12.27 |

TABLE 1-continued 2-(N-Cyanoimino)thiazolidin-4-ones

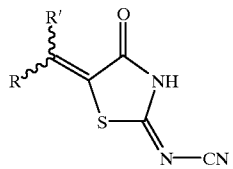

| 60 | 3060, 3040, 2950, 2775, 2195, 1730, 1685, 1590, 1505, 1310, 1270, 1230, 1095, 995, 730 | 2.22, 2.39(each 3H, s), 5.19(2H, s), 7.07(1H, s), 7.19(1H, s), 7.23–7.65(5H, m), 7.86(1H, s) | $C_{20}H_{17}N_3O_2S$ (363.441) | H 4.71, C 66.10, N 11.56 H 4.97, C 66.34, N 11.34 |
|---|---|---|---|---|
| 61 | 3060, 3020, 2930, 2827, 2765, 2189, 1716, 1592, 1519, 1334, 1250, 1216, 1173, 1027, 968, 833, 563, 539 | 2.71(3H, s), 3.78(3H, s), 6.75–7.85(10H, m) | $C_{21}H_{17}N_3O_2S \cdot \frac{1}{3}H_2O$ (381.457) | H 4.67, C 66.12, N 11.02 H 4.92, C 66.22, N 10.80 |

EXAMPLE 62

2-(N-Cyanoimino)-5-[(E)-4-stylylbenzylidene]thiazolidin-4-one Potassium Salt: Potassium Salt of the Compound of Example 1

The crude product (18.98 g) was recrystallized from 65% isopropanol to yield the title compound as yellow powder (10.87 g).

mp: >300° C. IR (KBr, cm$^{-1}$): 3025, 2180, 1750, 1590, 1490, 1420, 1340, 1290, 1205, 1180, 960, 820, 745, 540; $^1$H-NMR (DMSO-d6, ppm): δ 7.25–7.55 (6H, m), 7.55–7.85 (6H, m).

PHARMACOLOGICAL EXAMPLES

EXAMPLE 63

Hypotriglyceridemic Activity in Fructose-induced Hyperlipidemic Rats

The compounds were tested for a hypotriglyceridemic activity in fructose-induced hyperlipidemic rats in accordance with the method described in Nippon Yakurigaku Zasshi, 92 (3), 175–180 (1988). Sprague Dawley rats were divided into experimental groups with a comparable mean body weight. 75% fructose solution as drinking water was given to the animals for 7 days, while normal water was given to the intact groups ad libitum. During the experimental period the test compounds suspended in 3% gum arabic were given to the test group orally once a day in a daily dose of 30 mg/kg. The vehicle solution was given to the control group and the intact group. After 2 hours from the final administration, blood was collected from the abdominal aorta under ether anesthesia, and levels of total cholesterol and triglyceride in the serum were measured. The results are shown in Table 2. The reduction rate (%) was calculated according to the following equation:

Reduction rate (%) =

$$\left[1 - \frac{\text{(measured triglyceride level in each treated group)}}{\text{(measured triglyceride level in control group)}}\right] \times 100$$

Above experimental model is well known as a model of hypertriglicemia. As shown in Table 2, the compounds of the present invention have a serum trigriceride reducing activity.

TABLE 2

The hypotriglyceridemic activity in fructose induced hyperlipidemic rats

| Compound | Triglyceride (% Reduction) | Compound | Triglyceride (% Reduction) |
|---|---|---|---|
| Example 1 | 47 | Example 20 | 54 |
| Example 2 | 67 | Example 21 | 48 |
| Example 3 | 64 | Example 22 | 65 |
| Example 4 | 42 | Example 26 | 46 |
| Example 6 | 84 | Example 28 | 36 |
| Example 7 | 60 | Example 32 | 47 |
| Example 8 | 47 | Example 34 | 71 |
| Example 9 | 49 | Example 37 | 41 |
| Example 10 | 39 | Example 39 | 57 |
| Example 11 | 62 | Example 40 | 42 |
| Example 12 | 59 | Example 43 | 67 |
| Example 13 | 55 | Example 45 | 43 |
| Example 14 | 36 | Example 47 | 69 |
| Example 15 | 47 | Example 49 | 39 |
| Example 16 | 54 | Example 51 | 67 |
| Example 17 | 37 | Example 52 | 44 |
| Example 19 | 38 | | |

At a dose of 30 mg/kg p.o.

EXAMPLE 64

Lipid Lowering Effects in High Cholesterol-fed Hamsters

The compounds were tested for lipid lowering effects in high cholesterol-fed hamsters in accordance with the method described in Jpn Pharmacol Ther, 23 (suppl 4), s1047–1053 (1995). Male Syrian hamsters were fed the high cholesterol diet supplemented with 1% cholesterol and 10% coconut oil for 3 weeks. Before drug administration, blood was collected from the orbital venous plexus under ether anesthesia, and a serum total cholesterol level was measured. The animals were divided into groups so as to have a comparable mean total cholesterol level. The designated doses of the compound of Example 1 or Bezafibrate were administrated to test groups and the vehicle solution was given to the control group orally once a day for 7 days under the high cholesterol diet feeding. The intact group of animals were fed normal diet. After 4 hours of the final administration, blood was collected by cardiac puncture, and the total cholesterol and triglyceride levels in the serum were determined by the enzymatic method.

The results are shown in Table 3. The reduction rate (%) was calculated according to the following equation:

Reduction rate (%) =

$$\left[1 - \frac{\text{(measured lipid level in each treated group)}}{\text{(measured lipid level in control group)}}\right] \times 100$$

The result indicates that the compound of Example 1 has potent reducing activities in serum cholesterol and triglyceride levels and it is more effective than bezafibrate.

TABLE 3

Effect of the compound of Example 1 and bezafibrate on serum lipid levels in high cholesterol-fed hamsters

| Compound Activity Dose | Bezafibrate | | Compound of Example 1 | |
| --- | --- | --- | --- | --- |
| | Total cholesterol (% Reduction)* | Triglyceride (% Reduction)* | Total cholesterol (% Reduction) | Triglyceride (% Reduction) |
| 15 mg/kg | — | — | 26 | 60 |
| 30 mg/kg | −5 | −21 | 25 | 62 |
| 60 mg/kg | −0 | −18 | 29 | 69 |
| 120 mg/kg | 20 | 16 | 41 | 80 |

*A minus quantity represents the rate of increase.

EXAMPLE 65
Lipid Lowering Effects in High Cholesterol-fed Hamsters

The compounds of the present invention were evaluated for selecting more effective lipid lowering activities in the same manner described in Example 64 at a dose of 15 mg/kg p.o. The results are shown in Table 4. The reduction rate (%) was calculated according to the following equation:

Reduction rate (%) =

$$\left[1 - \frac{\text{(measured lipid level in each treated group)}}{\text{(measured lipid level in control group)}}\right] \times 100$$

TABLE 4

Hypolipidemic effects in high cholesterol-fed hamsters

| Compound | Total cholesterol (% Reduction) | Triglyceride (% Reduction) |
| --- | --- | --- |
| Example 2 | 27 | 57 |
| Example 3 | 16 | 17 |
| Example 7 | 18 | 12 |
| Example 9 | 15 | 15 |
| Example 14 | 11 | 24 |
| Example 15 | 32 | 61 |

At a dose of 15 mg/kg p.o.

EXAMPLE 66
Acute Toxicity

The single dose toxicity of the compound of Example 1 and Example 10 were evaluated after oral administration at a dose of 2000 mg/kg with each group comprising 3 mice. The animals were observed daily for 2 weeks after the administration. As a result, no deaths were observed.

EXAMPLE 67
Mutagenicity Test

The mutagenicity of the compound of Example 1 was examined by a reverse mutation test using *Salmonella typhimurium* TA100 and TA98 in the absence or presence of S9 mix. The compound of Example 1 did not increase the number of revertant colonies, and was not mutagenic in this test system.

What is claimed is:

1. Novel 2-(N-cyanoimino)thiazolidin-4-one derivatives represented by formula I or a pharmaceutically acceptable salt or solvate thereof:

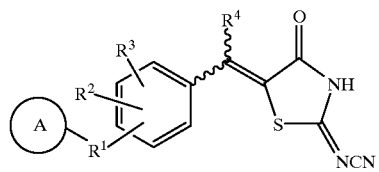

I wherein ring A represents a benzene ring, a condensed ring or a heterocyclic ring, each of which may be substituted by one or more substituents selected from a straight or branched $C_1$–$C_4$ alkyl group, a haloalkyl group, a halogen atom and —$OR^5$;

$R^1$ represents a single bond, an oxygen atom, a sulfur atom, a methyne group, a straight or branched $C_1$–$C_4$ alkylene or alkenylene group optionally substituted by a phenyl group, $R^6$—X, X—$R^6$, X—$R^6$—X, $R^6$—X—$R^6$, —C(=O)—$NR^7$— or —$NR^7$—C(=O)—;

$R^2$ and $R^3$ are the same or different and each represents a hydrogen atom, a $C_1$–$C_4$ alkyl group, —$OR^8$ or a halogen atom;

$R^4$ represents a hydrogen atom or a $C_1$–$C_4$ alkyl group;

$R^5$ represents a hydrogen atom or a $C_1$–$C_4$ alkyl group;

$R^6$ represents a straight or branched $C_1$–$C_4$ alkylene or alkenytene group;

$R^7$ represents a hydrogen atom or a $C_1$–$C_4$ alkyl group;

$R^8$ represents a hydrogen atom, a $C_1$–$C_4$ alkyl group or an aralkyl group;

X represents an oxygen atom or a sulfur atom.

2. Novel 2-(N-cyanoimino)thiazolidin-4-one derivatives or a pharmaceutically acceptable salt or solvate thereof according to claim 1, wherein ring A represents a benzene ring, a benzodioxole ring, a benzofuran ring, a benzothiazole, a fluorene ring, an indan ring, an indoline ring or a pyridine ring, each of which may be substituted by one or more substituents selected from a straight or branched $C_1$–$C_4$ alkyl group, a haloalkyl group, a halogen atom and —$OR^5$; $R^5$ represents a hydrogen atom or a $C_1$–$C_4$ alkyl group.

3. Novel 2-(N-cyanoimino)thiazolidin-4-one derivatives or a pharmaceutically acceptable salt or solvate thereof according to claim 1, wherein ring A represents a benzene ring which may be substituted by one or more substituents selected from a straight or branched $C_1$–$C_4$ alkyl group, a haloalkyl group, a halogen atom and —$OR^5$; $R^5$ represents a hydrogen atom or a $C_1$–$C_4$ alkyl group.

4. Novel 2-(N-cyanoimino)thiazolidin-4-one derivatives or a pharmaceutically acceptable salt or solvate thereof according to claim 1, wherein $R^1$ represents a methyne group or a straight or branched $C_1$–$C_4$ alkylene or alkenylene group optionally substituted by a phenyl group.

5. Novel 2-(N-cyanoimino)thiazolidin-4-one derivatives or a pharmaceutically acceptable salt or solvate thereof according to claim 1, wherein $R^1$ represents an oxygen atom or a sulfur atom.

6. Novel 2-(N-cyanoimino)thiazolidin-4-one derivatives or a pharmaceutically acceptable salt or solvate thereof according to claim 1, wherein $R^1$ represents a single bond.

7. Novel 2-(N-cyanoimino)thiazolidin-4-one derivatives or a pharmaceutically acceptable salt or solvate thereof according to claim 1, wherein $R^1$ represents $R^6$—X, X—$R^6$, X—$R^6$—X or $R^6$—X—$R^6$; $R^6$ represents a straight or branched $C_1$-$C_4$ alkylene or alkenylene group; X represents an oxygen atom or a sulfur atom.

8. Novel 2-(N-cyanoimino)thiazolidin-4-one derivatives or a pharmaceutically acceptable salt or solvate thereof according to claim 1, wherein $R^1$ represents —C(=O)—$NR^7$— or —$NR^7$—C(=O)—; $R^7$ represents a hydrogen atom or a $C_1$-$C_4$ alkyl group.

9. Novel 2-(N-cyanoimino)thiazolidin-4-one derivatives or a pharmaceutically acceptable salt or solvate thereof according to claim 1, wherein the compound of formula I is any one of the following:

2-(N-Cyanoimino)-5-[(E)-4-stylylbenzyidene]thiazolidin-4-one;

2-(N-Cyanoimino)-5-[(E)-4-(a-methylstylyl)benzylidene]thiazolidin-4-one;

2-(N-Cyanoimino)-5-[4-(benzyloxymethyl)benzylidene]thiazolidin-4-one;

2-(N-Cyanoimino)-5-[(E)-4-(b-methylstylyl)benzylidene]thiazolidin-4-one;

2-(N-Cyanoimino)-5-[4-(3-phenylpropoxy)benzylidene]thiazolidin-4-one;

2-(N-Cyanoimino)-5-[4-(4-chlorophenoxy)benzylidene]thiazolidin-4-one;

2-(N-Cyanoimino)-5-(4-phenylthiobenzylidene)thiazolidin-4-one;

2-(N-Cyanoimino)-5-[(E)-4-(2-fluorostylyl)benzylidene]thiazolidin-4-one;

2-(N-Cyanoimino)-5-[4-(2-dimethylphenoxy)benzylidene]thiazolidin-4-one;

2-(N-Cyanoimino)-5-(4-phenethyloxybenzylidene)thiazolidin-4-one;

2-(N-Cyanoimino)-5-[4-(2-phenylpropoxy)benzylidene]thiazolidin-4-one;

2-(N-Cyanoimino)-5-(3-phenethyloxybenzylidene)thiazolidin-4-one;

2-(N-Cyanoimino)-5-(4-benzyloxybenzylidene)thiazolidin-4-one;

2-(N-Cyanoimino)-5-[4-(5-chlorobenzofuran-2-yl)benzylidene]thiazolidin-4-one;

2-(N-Cyanoimino)-5-[(E)-4-(4-methoxystylyl)benzylidene]thiazolidin-4-one;

2-(N-Cyanoimino)-5-(3-phenoxybenzylidene)thiazolidin-4-one;

2-(N-Cyanoimino)-5-[4-(1,3-benzodioxol-5-ylmethoxy)benzylidene]thiazolidin-4-one;

2-(N-Cyanoimino)-5-[4-(4-methylbenzyloxy)benzylidene]thiazolidin-4-one;

2-(N-Cyanoimino)-5-[4-(4-chlorobenzyloxy)benzylidene]thiazolidin-4-one;

2-(N-Cyanoimino)-5-[3-methoxy-(E)-4-stylylbenzylidene]thiazolidin-4-one;

2-(N-Cyanoimino)-5-(2-phenethyloxybenzylidene)thiazolidin-4-one;

2-(N-Cyanoimino)-5-(4-phenoxybenzylidene)thiazolidin-4-one;

2-(N-Cyanoimino)-5-[3-(benzyloxy)benzylidene]thiazolidin-4-one;

2-(N-Cyanoimino)-5-[4-(benzylthio)benzylidene]thiazolidin-4-one;

2-(N-Cyanoimino)-5-(4-phenethylbenzylidene)thiazolidin-4-one;

2-(N-Cyanoimino)-5-[4-[2-(4-chlorophenyl)ethoxy]benzylidene]thiazolidin-4-one;

2-(N-Cyanoimino)-5-[1-[(E)-4-(4-methoxystylyl)phenyl]ethylidene]thiazolidin-4-one;

2-(N-Cyanoimino)-5-(4-benzyloxy-2,5-dimethylbenzylidene)thiazolidin-4-one; or 2-(N-Cyanoimino)-5-[(E)-3-stylylbenzylidene]thiazolidin-4-one.

10. A process for preparing a 2-(N-cyanoimino)thiazolidin-4-one derivatives or a pharmaceutically acceptable salt or solvate thereof according to claim 1, which comprises reacting a compound represented by formula II, or salts thereof, with an aldehyde or ketone represented by formula III:

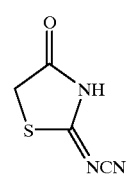

II

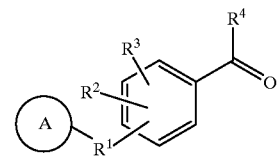

III wherein ring A represents a benzene ring, a condensed ring or a heterocyclic ring, each of which may be substituted by one or more substituents selected from a straight or branched $C_1$-$C_4$ alkyl group, a haloalkyl group, a halogen atom and —$OR^5$;

$R^1$ represents a single bond, an oxygen atom, a sulfur atom, a methyne group, a straight or branched $C_1$-$C_4$ alkylene or alkenylene group optionally substituted by a phenyl group, $R^6$—X, X—$R^6$, X—$R^6$—X, $R^6$—X—$R^6$, —C(=O)—$NR^7$— or —$NR^7$—C(=O)—;

$R^2$ and $R^3$ are the same or different and each represents a hydrogen atom, a $C_1$-$C_4$ alkyl group, —$OR^8$ or a halogen atom;

$R^4$ represents a hydrogen atom or a $C_1$-$C_4$ alkyl group;

$R^5$ represents a hydrogen atom or a $C_1$-$C_4$ alkyl group;

$R^6$ represents a straight or branched $C_1$-$C_4$ alkylene or alkenylene group;

$R^7$ represents a hydrogen atom or a $C_1$-$C_4$ alkyl group;

$R^8$ represents a hydrogen atom, a $C_1$-$C_4$ alkyl group or an aralkyl group;

X represents an oxygen atom or a sulfur atom.

11. A pharmaceutical composition for treating hyperlipidemia comprising novel 2-(N-cyanoimino)thiazolidin-4-one derivatives and/or a pharmaceutically acceptable salt and/or solvate thereof according to claim 1 as an active ingredient and a pharmaceutically acceptable carrier.

12. A pharmaceutical composition for treating hyperlipidemia comprising novel 2-(N-cyanoimino)thiazolidin-4-one derivatives and/or a pharmaceutically acceptable salt and/or solvate thereof according to claim 2 as an active ingredient and a pharmaceutically acceptable carrier.

13. A pharmaceutical composition for treating hyperlipidemia comprising novel 2-(N-cyanoimino)thiazolidin-4-one derivatives and/or a pharmaceutically acceptable salt and/or solvate thereof according to claim 3 as an active ingredient and a pharmaceutically acceptable carrier.

14. A pharmaceutical composition for treating hyperlipidemia comprising novel 2-(N-cyanoimino)thiazolidin-4-one derivatives and/or a pharmaceutically acceptable salt and/or solvate thereof according to claim 4 as an active ingredient and a pharmaceutically acceptable carrier.

15. A pharmaceutical composition for treating hyperlipidemia comprising novel 2-(N-cyanoimino)thiazolidin-4-one derivatives and/or a pharmaceutically acceptable salt and/or solvate thereof according to claim 5 as an active ingredient and a pharmaceutically acceptable carrier.

16. A pharmaceutical composition for treating hyperlipidemia comprising novel 2-(N-cyanoimino)thiazolidin-4-one derivatives and/or a pharmaceutically acceptable salt and/or solvate thereof according to claim 6 as an active ingredient and a pharmaceutically acceptable carrier.

17. A pharmaceutical composition for treating hyperlipidemia comprising novel 2-(N-cyanoimino)thiazolidin-4-one derivatives and/or a pharmaceutically acceptable salt and/or solvate thereof according to claim 7 as an active ingredient and a pharmaceutically acceptable carrier.

18. A pharmaceutical composition for treating hyperlipidemia comprising novel 2-(N-cyanoimino)thiazolidin-4-one derivatives and/or a pharmaceutically acceptable salt and/or solvate thereof according to claim 8 as an active ingredient and a pharmaceutically acceptable carrier.

19. A pharmaceutical composition for treating hyperlipidemia comprising novel 2-(N-cyanoimino)thiazolidin-4-one derivatives and/or a pharmaceutically acceptable salt and/or solvate thereof according to claim 9 as an active ingredient and a pharmaceutically acceptable carrier.

* * * * *